(12) United States Patent
Farley

(10) Patent No.: US 6,607,755 B2
(45) Date of Patent: Aug. 19, 2003

(54) ANTI-AROMATASE PHARMACEUTICAL COMPOSITION FOR CONTROLLING TESTOSTERONE/ESTRONE RATIOS

(76) Inventor: Michael Donald Farley, 255 5th Ave., Suite 6, Indialantic, FL (US) 32903

( * ) Notice: Subject to any disclaimer, the term of this patent is extended or adjusted under 35 U.S.C. 154(b) by 0 days.

(21) Appl. No.: 09/921,018

(22) Filed: Jun. 21, 2001

(65) Prior Publication Data

US 2003/0099728 A1 May 29, 2003

(51) Int. Cl.[7] .............................................. A61K 35/78
(52) U.S. Cl. ........................ 424/735; 424/725; 424/775
(58) Field of Search .................. 424/735, 410, 424/775, 725; 435/195.1

(56) References Cited

U.S. PATENT DOCUMENTS

| | | | |
|---|---|---|---|
| 4,598,072 A | 7/1986 | Schweibert ................ | 514/170 |
| 5,284,873 A * | 2/1994 | Salinero-Rodero et al. . | 514/558 |
| 5,861,389 A | 1/1999 | Radlmeier .................. | 514/177 |
| 5,972,921 A | 10/1999 | Santti ......................... | 514/177 |
| 6,039,950 A * | 3/2000 | Khwaija et al. ......... | 424/195.1 |
| 2001/0008638 A1 * | 7/2001 | Wilding ...................... | 424/468 |

* cited by examiner

Primary Examiner—David M. Naff
Assistant Examiner—Deborah K Ware
(74) Attorney, Agent, or Firm—Transnational Enterprise; Bidyut K. Niyogi

(57) ABSTRACT

An anti-aromatase pharmaceutical composition is provided containing nettle root extract in the range of about 275 to 350 mg, pumpkin seed oil in the range of about 150 to 205 mg, Pygeum Africanum or Prunus africana bark extract, standardized to contain at least 12 to 15% of total sterols, in the range of about 20 to 40 mg, and Chrysin in the range of 475 to 550 mg. This pharmaceutical composition assists in the treatment of benign prostate hyperthropy and breast cancer.

5 Claims, No Drawings

ANTI-AROMATASE PHARMACEUTICAL COMPOSITION FOR CONTROLLING TESTOSTERONE/ESTRONE RATIOS

It is known, that throughout life of a mammal or a human being, testosterone/estrone ratios do have a considerable effect on mammal or human life.

This testosterone/estrone ratio will exert a powerful and considerable reactions to the emotional well being, as well as in sexual functions, libido, muscle mass and strength, energy, cardiovascular health, bone integrity and memory behavior.

It is advantageous that testosterone/estrogen ratio is directly influenced by the aromitazation and bioavailable levels of several other hormones, including DHEA projesterone, androstenedione, estrone aldosterone, cortisol, The present invention includes an anti-aromatase pharmaceutical composition in dose compound form comprising a formula in which each capsule or dose consists of:

a. Nettle root extract (Ustica dioica) 16:1 in the range of about 275 to above 350 mg.;

b. Pumpkin seed oil (cucubita pepo) in the range of about 150 mg. to about 205 mg.;

c. Pygeum Africanum (Prunus africana) bark extract standardized to contain about 12 to 14 % of total sterols in the range of about 20 mg. to about 40 mg.; and d. Chrysin in the range of about 475 mg. to about 550 mg.

However, the present invention also relates to a totally new use of a male hormone panel aromatasition structure with an androgen pathway as depicted at table I and II, also for breast cancer and other related treatments.

TABLE I

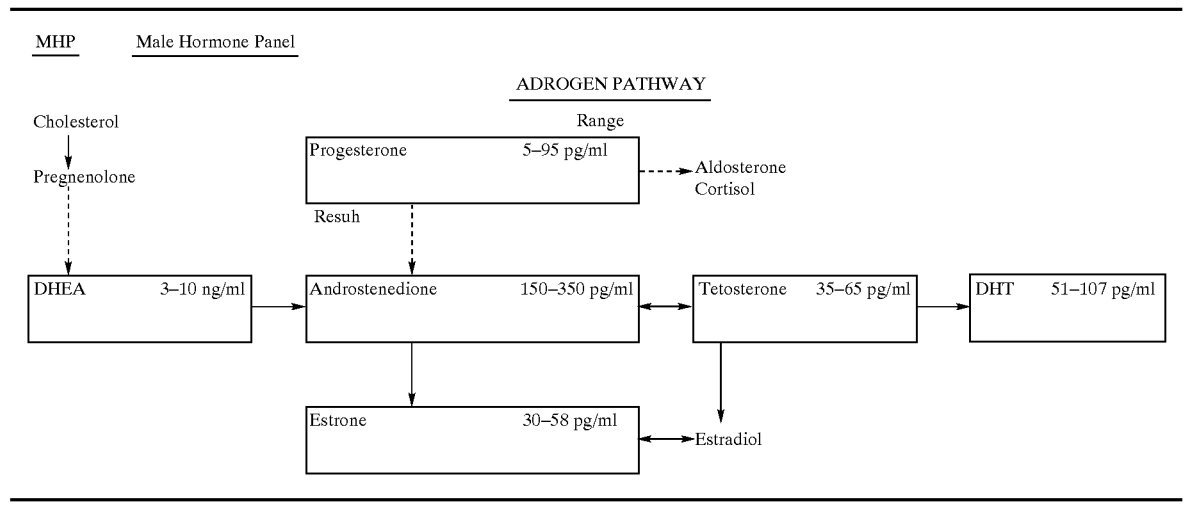

estradiol and dihydrotestoasterone. These hormones which directly effect testosterone and estrogen ratios, also directly effect emotional well being, as well as sexual function, libido, muscle mass, fat to lean muscle ratios, strength, energy, cardiovascular health, osteoporosis, memory and cognitive function, as well as risk for breast cancer and benign prostate hypertrophy.

It is well established, that as a human being ages, these testosterone/estrone ratios adjust and change with age, with increasing formation levels of estrone and a proportional decrease in the formation of testosterone.

It is known for the specification of U.S. Pat. No. 4,598,072 to Schweibert etal dated Jul. 1, 1986 to provide for an aromatase inhibitor and an antiandrogen which generally is applicable for the treatment of prostatic hyperglania, incorporated herein by reference only.

Furthermore, it is known for the specification of U.S. Pat. No. 5,972,921 to Santti et.al dated Oct. 26, 1999 in the use of an aromatase inhibitor administered for the specific treatment for men for detrusor wrethral dyssynergia. This is in corporated herein for reference only.

It is also known for the specification of U.S. Pat. No. 5,861,389 to Radlmaier et.al dated Jan. 19,1999 for specific treatment of only androgen deficiency in men using selective aromatase inhibitors. This is in corporated herein for reference only.

TABLE II

Normal Range of Hormone Values
Reference Ranges

| Hormone | Range | Age |
|---|---|---|
| Testosterone (Male) | 70–135 | >20 yrs |
| | 60–110 | 20–30 yrs |
| | 50–80 | 31–40 yrs |
| | 40–70 | 41–50 yrs |
| | 35–65 | 51–60 yrs |
| | 20–55 | 61–70 yrs |
| | 15–45 | >70 yrs |
| Dihydrotestosterone (Male) | 22–72 | 30–39 yrs |
| | 52–123 | 40–49 yrs |
| | 51–107 | 50–59 yrs |
| | 39–89 | >60 yrs |
| Androstenedione (Male) | 100–150 | } >15 yrs |
| | 151–350 | |
| | 351–450 | |
| Estrone (Female) | 38–68 | 40–49 yrs |
| | 26–64 | 50–59 yrs |
| | 35–65 | >60 yrs |

Both Tables I and II depict Aromatisation structure that are beneficial to the method of treatment of various ailments, for example, benign prostate hyperthrophy, some forms of breast cancer, and in the treatment of osteoporsis, etc.

Specifically the present invention relates to a totally new application of several naturally occurring aromatase inhibitors which interupt several stages in the presented hormone panel (Table 1), which illustrates the currently accepted normal aromatization sequence. This invention also incorporates for the first time, an inhibitor of sex hormone binding globulin which allows bioavailable hormone to remain active at target tissue sites for a longer period of time.

Suitably, the present invention includes an anti-aromatase capsule or dose in compound form in which the pharmaceutical composition consists of:

a. Nettle root extract (Uritica dioica) 16:1 of about 300 mg.;
b. Pumpkin seed oil (Cucubita pepo) in the range of about 150 mg. to about 205 mg.;
c. Pygeum Africanum (Prunus africana) bark extract standardized to contain about 12 to 14 % of total sterols in the range of about 20 mg. to about 40 mg.; and
d. Chrysin in the range of about 475 mg. to about 550 mg.

Conveniently, this invention is an anti-aromatase capsule or dose in compound form in which the pharmacuetical composition consists of:

a. Pumpkin seed oil (Cucubita pepo) of about 175 mg.;
b. Nettle root extract (Uritica dioica) 16:1 of about 300 mg.;
c. Pygeum Africanum (Prunus africana) bark extract standardized to contain 12 to 14% of total sterols in the range of about 20 mg. to about 40 mg.; and
d. Chrysin in the range of about 475 mg. to about 550 mg.

Advantageously, this invention resides in an anti-aromatase capsule or dose in compound form in which the pharmaceutical composition consists of:

a. Pygeum Africanum (Prunus africana) bark extract standardized to contain 13% total sterols and about 25 mg.;
b. Pumpkin seed oil (Cucubita pepo) of about 175 mg.;
c. Nettle root extract (Urtica dioica) 16:1 of about 300 mg; and
d. Chrysin in the range of about 475 mg. to about 550 mg.

Moreover, the present invention is an anti-aromatase capsule or dose in compound form comprising a formula in the pharmaceutical composition of which each capsule or dose consists of:

a. Chyrsin of about 500 mg;
b. Nettle root extract (Urtica dioica) of about 300 mg.;
c. Pumpkin seed oil (Cucubita pepo) of about 175 mg.; and
d. Pygeum Africanum (Prunus africana) bark extract standardized to contain 13% total sterols and about 25 mg.

In addition, the invention resides in a method of treatment utilizing a pharmaceutical composition consisting of a dosage or capsule constituted by an anti-aromatase pharmaceutical composition in dose compound form comprising a formula in which each capsule or dose consists of:

(a) Nettle root extract Iustica dioica) 16:1 in the range of about 275 to above 350 mg.;
(b) Pumpkin seed oil (cucubita pepo) in the range of about 150 mg. to about 205 mg.;
(c) Pygeum Africanum (Prunus africana) bark extract standardized to contain about 12 to 14 % of total sterols in the range of about 20 mg. to about 40 mg.; and
(d) Chrysin in the range of about 475 mg. to about 550 mg.

Also, the invention provides a method of treatment utilizing a pharmaceutical composition consisting of a dosage or capsule constituted an anti-aromatase capsule or dose in compound form in which the pharmaceutical composition consists of:

(a) Nettle root extract (Uritica dioica) 16:1 of about 300 mg.;
(b) Pumpkin seed oil (Cucubita pepo) in the range of about 150 mg. to about 205 mg.;
(c) Pygeum Africanum (Prunus africana) bark extract standardized to contain about 12 to 14 % of total sterols in the range of about 20 mg. to about 40 mg.; and
(d) Chrysin in the range of about 475 mg. to about 550 mg.

Furthermore, the invention assists a method of treatment utilizing a pharmaceutical composition consisting of a dosage or capsule constituted an anti-aromatase capsule or dose compound form in which the pharmaceutical composition consists of:

(a) Pumpkin seed oil (Cucubita pepo) of about 175 mg.;
(b) Nettle root extract (Uritica dioica) 16:1 of about 300 mg.;
(c) Pygeum Africanum (Prunus africana) bark extract standardized to contain 12 to 14% of total sterols in the range of about 20 mg. to about
(d) Chrysin in the range of about 475 mg. to about 550 mg.

The invention also includes a method of treatment utilizing a pharmaceutical composition consisting of a dosage or capsule constituted an anti-aromatase capsule or dose in compound form in which the pharmaceutical composition consists of:

(a) Pygeum Africanum (Prunus africana) bark extract standardized to contain 13% total sterols and about 25 mg.;
(b) Pumpkin seed oil (Cucubita pepo) of about 175 mg.;
(c) Nettle root extract (Urtica dioica) 16:1 of about 300 mg; and
(d) Chrysin in the range of about 475 mg. to about 550 mg.

The invention furthermore includes a method of treatment utilizing a pharmaceutical composition consisting of a dosage or capsule constituted by an anti-aromatase capsule or dose in compound form comprising a formula in the pharmaceutical composition of which each capsule or dose consists of:

(a) Chyrsin of about 500 mg;
(b) Nettle root extract (Urtica dioica) of about 300 mg.;
(c) Pumpkin seed oil (Cucubita pepo) of about 175 mg.; and
(d) Pygeum Africanum (Prunus africana) bark extract standardized to contain 13% total sterols and about 25 mg.

An anti-aromatase pharmaceutical composition, consisting of in capsule or dose to contain:

Nettle root extract (Urtica dioica) 16:1 in the range of about 275 to 350 mg.
Pumpkin seed oil (Cucubita pepo) in the range of about 150 to 205 mg.
Pygeum Africanum (Prunus africana) bark extract standardized to contain at least 12 to 15% of total sterols in the range of about 20 to 40 mg. and
Chrysin in the range of 475 to 550 mg.

This pharmaceutical composition assists in the treatment of benign prostate hyperthropy and breast cancer etc.

I claim:

1. An anti-aromatase pharmaceutical composition for maintaining testosterone/estrone ratios comprising:
   (a) Nettle root extract of about 275 to 350 mg;
   (b) Pumpkin seed oil of about 150 mg, to 205 mg;
   (c) Pygeum Africanum or Prunus africana bark extract, standardized to contain about 12 to 14% of total sterols, of about 20 mg, to 40 mg; and
   (d) Chrysin of about 475 mg, to 550 mg.

2. The anti-aromatase composition as claimed in claim 1 wherein the Nettle root extract of about 300 mg.

3. The anti-aromatase composition as claimed in claim 2 wherein the pumpkin seed oil of about 175 mg.

4. The anti-aromatase composition as claimed in claim 3 wherein the Pygeum Africanum or Prunus africana bark extract, standardized to contain 13% total sterols of about 25 mg.

5. The anti-aromatase composition as claimed in claim 4 wherein the Chyrsin is about 500 mg.

* * * * *